United States Patent [19]

Hampar et al.

[11] Patent Number: 4,764,459
[45] Date of Patent: Aug. 16, 1988

[54] ENZYME-LINKED IMMUNOSORBENT ASSAY (ELISA) FOR DETERMINING ANTI-BODIES AGAINST HERPES SIMPLEX VIRUS (HSV) TYPES 1 AND 2 IN HUMAN SERA

[75] Inventors: Berge Hampar, Middletown; Stephen D. Showalter, Gaithersburg; Martin Zweig, Walkersville, all of Md.

[73] Assignee: The United States of America as represented by the Department of Health and Human Services, Washington, D.C.

[21] Appl. No.: 687,370

[22] Filed: Dec. 28, 1984

[51] Int. Cl.[4] .................. C12Q 1/70; G01N 33/571; G01N 33/577
[52] U.S. Cl. ........................... 435/5; 435/810; 436/511; 436/548; 436/809; 436/825
[58] Field of Search .............. 435/5, 7, 28, 810; 436/511, 518, 531, 548, 809, 825

[56] References Cited
U.S. PATENT DOCUMENTS 4,430,437  2/1984  Hampar et al. ............... 436/548
4,446,232  5/1984  Liotta ............................ 435/7
4,450,231  5/1984  Ozkan ........................... 435/7
4,535,057  8/1985  Dreesman et al. ............. 435/5
4,572,896  2/1986  Hampar et al. ............. 435/172.2

OTHER PUBLICATIONS

Zweig et al., "J. of Virology" vol. 47, No. 1, (Jul. 1983), pp. 185–192.
Showalter et al., "Infec. and Immun." vol. 34, No. 3, (Dec. 1981), pp. 684–692.

Primary Examiner—Esther M. Kepplinger
Attorney, Agent, or Firm—John S. Roberts, Jr.

[57] ABSTRACT

A method and test kit for the serological diagnosis of human infection by herpes sipmlex virus type 1 (HSV-1) and herpes simplex virus type 2 (HSV-2) using immunoaffinity purified virus-coded glycoproteins as target antigens. A preferred embodiment of the method employs a variation of the enzyme-linked immunosorbent assay (ELISA) whereby monoclonal antibodies are used to purify target antigens, and test sera are absorbed with virus-infected cell extracts to remove intertypic cross-reacting antibodies.

9 Claims, 1 Drawing Sheet

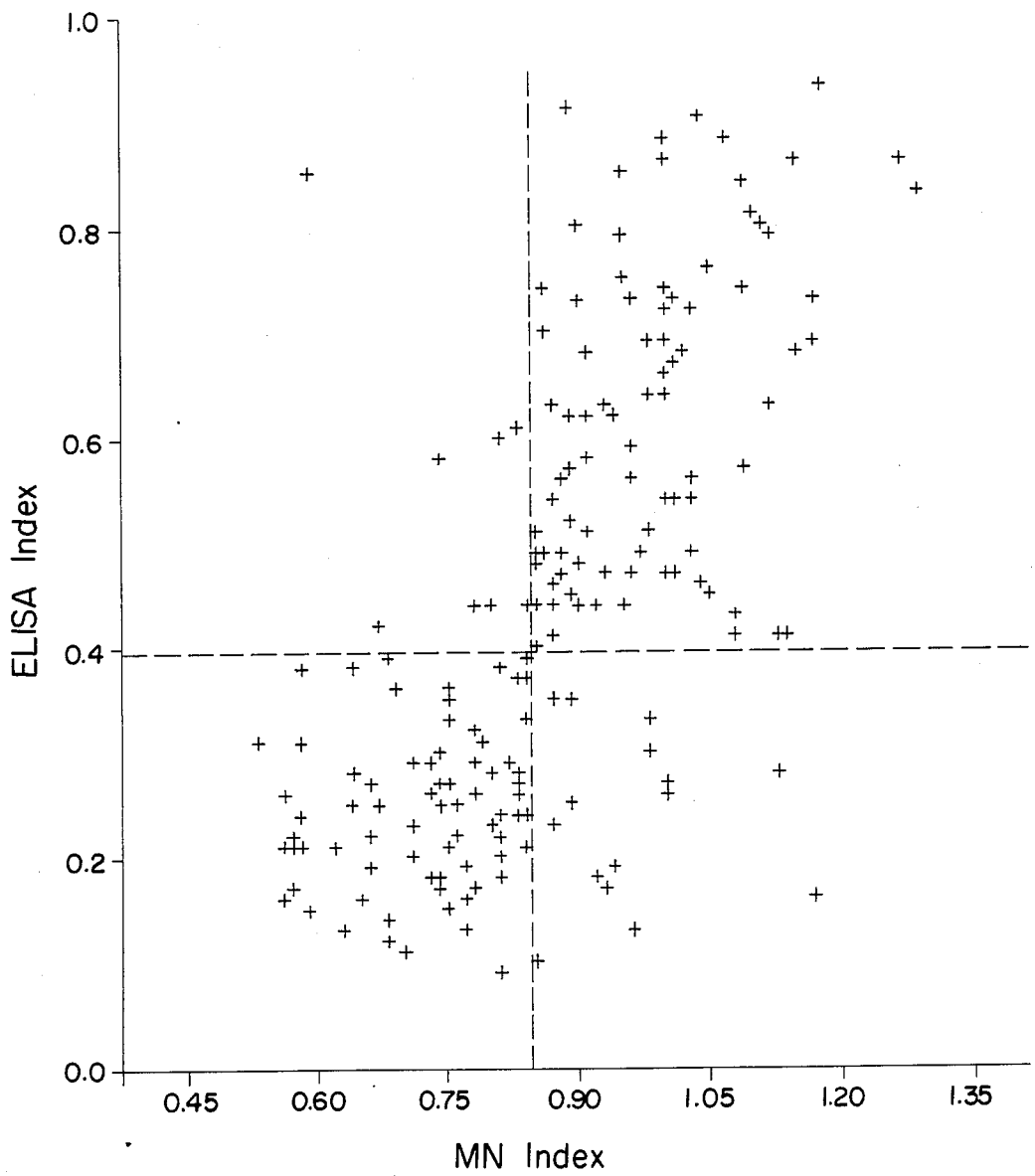

ENZYME-LINKED IMMUNOSORBENT ASSAY (ELISA) FOR DETERMINING ANTI-BODIES AGAINST HERPES SIMPLEX VIRUS (HSV) TYPES 1 AND 2 IN HUMAN SERA

A rapid and reproducible enzyme-linked immunosorbent assay (ELISA) is disclosed for determining antibodies in human sera against herpes simplex virus type 1 (HSV-1) and type 2 (HSV-2). Test sera are absorbed with heterologous virus-infected cell extracts to remove cross-reacting antibodies and applied to microtiter plates containing the target antigens, immunoaffinity purified HSV-1 glycoproteins and HSV-2 glycoproteins. The preferred glycoproteins are HSV-1 glycoproteins C (gC) and D (gD) and HSV-2 glycoproteins D (gD) and F (gF). These glycoproteins are purified by an immunoaffinity process using monoclonal antibodies.

BACKGROUND OF THE INVENTION

Herpes simplex virus (HSV) is widespread in the human population, and is considered a classic example of a "latent" virus. Two major forms of infection are recognized. Primary or systemic HSV infection occurs in individuals lacking antibodies to HSV. Recurrent HSV infection, believed to result from activation of "latent" virus, occurs at localized sites in individuals expressing antibodies. A third form, which occurs at a lower frequency, is seen in previously infected individuals whose immune system is compromised, thus allowing virus replication and systemic infection.

Two types of HSV are recognized; HSV-1, which usually is associated with infections in the oral region, and HSV-2, which usually is associated with infections in the genital region. Although antibodies generated against HSV-1 and HSV-2 show extensive intertypic cross-reactivity (see Hampar et al., J. Immunol., Vol. 104, p 593 (1970)), the two virus types can be distinguished by their antigenic profiles and by their genetic composition. While most adults express protective antibodies against HSV, primary or systemic infection can pose a serious problem. In newborns, for example, a potentially fatal infection can occur following transmission of virus from mothers with an active recurrent genital infection. During the past 20 years, in fact, the incidence of neonatal HSV infection has increased significantly in parallel with the increased incidence of genital HSV infection in pregnant females (approximately a nine-fold increase from 1966 to 1979). Systemic HSV infection during pregnancy is also potentially dangerous to the mother.

The recommended procedure for a pregnant woman suspected of harboring a genital HSV infection is to perform weekly tests to determine whether infectious virus is being released into the birth canal. This is a costly and insensitive procedure, however, and its use is limited to the high risk category of pregnant women who show either (i) a history of recurrent genital HSV infection, (ii) active disease during pregnancy, or (iii) sexual partners with proven genital HSV infection. If an active infection is apparent, a cesarean delivery, with its associated risks, is performed to protect the newborn. Unfortunately, approximately 70% of neonates with HSV infection are born of women with no clinical signs or symptoms of active disease. Consequently, the availability of a rapid, reliable and inexpensive serological test for identifying women harboring HSV-2 is needed.

Infection by HSV-1 and HSV-2 can occur in any area of the body. While recurrent infection in the genital area usually involves HSV-2, the high incidence of HSV antibodies in the adult population is primarily due to HSV-1, which usually is associated with oral infections. While HSV-1 and HSV-2 are closely related antigenically, a number of serological tests have been developed for differentiating between antibodies directed against the two virus types.

These tests include, inter alia, neutralization kinetics (NK), multiplicity analysis NK, microneutralization (MN), modified MN, indirect hemagglutination, immune lysis of infected cells, radioimmunoassay using purified viral proteins, immunoelectrophoresis, radioimmunoprecipitation-polyacrylamide gel electrophoresis, and enzyme-linked immunosorbent assay (ELISA). The MN and modified MN tests are the most widely used tests for distinguishing between antibodies directed against HSV-1 and HSV-2, and are considered the standard against which any new test should be compared.

In intital attempts to develop an ELISA test for distinguishing between antibodies directed against HSV-1 and HSV-2, it was assumed from other studies that the 130,000 mw glycoprotein C (gC) was antigenically specific for HSV-1. Initial attempts were unsuccessful, however, since positive ELISA reactions were consistently observed when HSV-2 specific antisera were tested against affinity purified gC. It was subsequently shown that gC was not specific for HSV-1, but was antigenically cross-reactive and mapped at a position colinear with the 75,000 mw glycoprotein F (gF) of HSV-2 (see Zweig et al., J. Virol. Vol. 47 p 185 (1983)). Glycoprotein gD is 110,000 mw. A confirmed antigenically type-specific protein has not been described for either HSV-1 or HSV-2. The present invention is designed to develop an immunoassay method which can be used effectively for differentiating antibodies directed against HSV-1 and HSV-2 in human sera. The results of these efforts comprise the invention described herein.

SUMMARY OF THE INVENTION

This invention relates to an immunoassay method for distinguishing between antibodies directed against HSV-1 and HSV-2 in human serum. More specifically, the invention relates to a method whereby purified highly immunogenic glycoproteins encoded by HSV-1 (gC and gD) and HSV-2 (gD and gF) are used as target antigens in a variation of the enzyme-linked immunosorbent assay (ELISA). A preferred embodiment of the method employs monoclonal antibodies for immunoaffinity purification of target antigens, although other purification procedures will work equally as well. Mixtures comprising purified HSV-1 gC and gD and purified HSV-2 gD and gF are attached to wells of microtiter plates to serve as target antigens. Other purified HSV-1 and HSV-2 glycoproteins, singly or in combination, will serve equally as well.

A relatively simple procedure utilizing heterologous virus-infected cell extracts is employed for absorption of human sera to remove intertypic cross-reactive antibodies. Theoretically, the absorption step may be eliminated if an antigenically type-specific HSV-1 or HSV-2 protein or a peptide target antigen containing one or more type-specific epitope becomes available.

The absorbed human serum is added to microtiter plate wells containing either HSV-1 or HSV-2 target antigens to produce an antigen-antibody immune complex. The wells are washed to remove unbound antibody, and an enzyme-conjugated anti-human immunoglobulin is added. The wells are washed and a color producing substrate solution is added. The absorbance index (ELISA Index), defined as the ratio of absorbance generated by a serum sample absorbed with an heterologous virus-infected cell extract vs. a serum sample absorbed with an uninfected cell extract, is used to determine the presence or absence of antibodies directed against HSV-1 and HSV-2.

Any immumunoassay method which measures the binding of antibody to a target antigen can be employed to practice the invention.

DESCRIPTION OF THE FIGURE

The FIGURE is a scatter diagram of results of sera analyzed for antibodies to HSV-2 by the ELISA test and the modified microneutralization MN test. The ELISA Index is defined below. The MN Index is the II/I neutralization index described by Rawls et al, *J. Immunol.*, Vol. 104, 599–606 (1970). The broken lines at an ELISA Index of 0.395 and a MN index of 0.845 represent the borders between negative and positive values for antibodies against HSV-2. The Pearson correlation coefficient (r) is 0.64, $p<0.0001$. A number of sera could not be plotted since specific x-y coordinates were not obtained; results of assays for these sera were recorded simply as "less than" or "greater than." The great majority of these sera would fall in the lower left quadrant of the graph, indicating a negative diagnosis by both tests.

MATERIAL INFORMATION DISCLOSURE

David et al (U.S. Pat. No. 4,376,110) discloses a sandwich-type immunoassay using two monoclonal antibodies.

Liotta (U.S. Pat. No. 4,446,232) discloses an ELISA assay device and procedure consisting of a two-zoned reaction area.

Hampar et al. (U.S. Pat. No. 4,430,437) discloses assay techniques for the diagnosis of herpes simplex virus 1 and 2 using monoclonal antibodies.

Showalter et al, *Infection and Immunity*, Vol. 34, pp 684–692 (1981) and Zweig et al, *Journal of Virology*, Vol. 47, pp 185–192 (1983) disclose some of the glycoproteins of HSV-I and HSV-2, and the preparation of monoclonal antibodies against HSV-I and HSV-2 proteins.

SPECIFIC DISCLOSURE

The present invention is a method for determining the presence of antigens directed against HSV-1 and HSV-2 in a biological fluid consisting essentially of a modified enzyme-linked immunoabsorbent assay (ELISA). The present invention is an improvement of existing ELISA and other tests for distinguishing HSV-1 and HSV-2 antibodies. The improvements consist of the use of monoclonal antibody immunoaffinity purified target antigens encoded by HSV-1 and HSV-2, a simplified procedure for absorbing human serum for removal of intertypic cross-reacting antibodies, and the rapidity, cost-effectiveness and reliability of the test.

A more detailed description of the above process follows.

Infected Cell Extracts

Vero cells are grown in roller bottles (850 cm$^2$) using Eagle's minimal essential medium supplemented with 10% heat-inactivated fetal calf serum, penicillin and streptomycin. The cells are infected with either HSV-1 (strain 14012) or HSV-2 (strain 333) for 1 hr at 37° C. using a multiplicity of infection (moi) of 10–20. The inoculum is removed, fresh medium containing 5% fetal calf serum is added, the cells are incubated for an additional 24 hrs, and then harvested by sedimentation.

Five ml of packed infected cells harvested from 20 roller bottles are resuspended with 15-ml of extraction buffer [0.1 M Tris-hydrochloride (pH 8.0)-10% glycerol - 0.5% sodium deoxycholate - 0.5% Nonidet P-40 - 0.2 mM phenylmethylsulfonyl chloride - 1% Aprotinin (Sigma Chemical Co.)] by mixing for 1 hr at 4° C. on a rotator. The cells are disrupted by sonication and clarified by centrifugation at 40,000 x g for 1 hr at 4° C. The supernatant fluids (infected cell extracts) are harvested and stored in aliquots at $-70°$ C.

Purification of Monoclonal Antibodies

The following previously described monoclonal antibodies (cf Showalter and Zweig in Material Information Disclosure) are employed: 4S, which reacts with gD from HSV-1 and HSV-2; 19S, which reacts with HSV-1 gC; and 104S, which reacts with HSV-2 gF and HSV-1 gC. These antibodies have been placed on deposit with the American Type Culture Collection (ATCC) before the filing of this application. This invention is not limited to the named antibodies but only to antibodies targeted to the HSV glycoprotein antigens. The following journal articles are incorporated by reference as describing the battery of monoclonal antibodies that may be used: Showalter et al, *Inf. Immun.*, Vol. 34, pp 684–692 (1981) and Zweig et al, *J. Virol.*, Vol. 47, pp 185–192 (1983). The references above indicate that these monoclonal antibodies (MAB) were known and used in research and commercial lots since about 1980.

For purification of monoclonal antibody 104-S, ascites fluid (10-15 ml) is dialyzed extensively against 20 mM Tris-hydrochloride (pH 7.2) and is clarified by filtration through glass wool and centrifugation at 6,000 rpm for 10 minutes at 4° C. The fluid is then applied to a 2.5×20 cm column of DEAE Affi-Gel Blue (Bio Rad Laboratories, Richmond, Calif.) (bed vol.=100 ml) at 4° C., and the column is washed with 300 ml of 20 mM Tris-hydrochloride, (pH 7.2), and then with 300 ml of 25 mM NaCl - 20 mM Tris-hydrochloride (pH 7.2). Immunoglobulin is eluted in approximately 60 ml of the 300 ml of 50 mM NaCl - 20 mM Tris-hydrochloride (pH 7.2) added to the column. The remaining proteins are eluted with 300 ml of 1.4 M NaCl - Tris-hydrochloride (pH 7.2). Analysis by SDS-polyacrylamide gel electrophoresis indicates approximately an 80-90% purity of the immunoglobulin fraction, with minor contamination with transferrin. The total immunoglobulin protein recovered, as measured by the Bio Rad Protein Assay (Bio-Rad Laboratories), is 3 mg.

For monoclonal antibodies 4S and 19S, clarified ascites fluids (approximately 14 ml) are dialyzed extensively against 0.14 M sodium phosphate buffer (pH 8.0) and mixed with protein A-Sepharose CL-4B beads (Pharmacia Fine Chemicals, Inc.) for 1 hr at 4° C. The beads are washed four times with PBS (pH 8.0), loaded into a Bio Rad polypropylene column (Bio-Rad Laboratories), washed with PBS (pH 8.0), and then washed with 0.1 M sodium phosphate buffer (pH 7.2). Immunoglobulins are eluted with 0.1 M sodium citrate buffer (pH 3.0) and are dialyzed against 0.5 M NaCl-0.2 M sodium bicarbonate buffer (pH 8.5). The purity of the immunoglobulin preparations are determined by SDS-polyacrylamide gel electrophoresis as described (see Zweig et al., *J. Virol.* Vol 47 p 185 (1983)), and the protein yields determined by the Bio Rad Protein Assay (Bio-Rad Laboratories).

Purification of Viral Antigens gD and gC are purified from HSV-1 infected cell extracts, and gD and gF are purified from HSV-2 infected cell extracts by immunoaffinity chromatography (see Zweig et al., supra). Monoclonal antibody 4S is used for purification of HSV-1 gD and HSV-2 gD, monoclonal antibody 19S is used for purification of HSV-1 gC, and monoclonal antibody 104S is used for purification of HSV-2 gF.

Purified immunoglobulin is coupled to CNBr-activated Sepharose 4B beads (Pharmacia Fine Chemicals, Inc.) at 5 mg of protein per ml of gel, in accordance with the instructions of the manufacturer. The antibody-coupled beads are washed three times with extraction buffer, and 0.5 ml portions are mixed with 15 ml of infected cell extract on a rotator at 4° C. for 90 min. The beads are pelleted (1,000 x g, 3 min.), washed three times with 10 ml of extraction buffer, and antigen is released by resuspending the beads in 2-3 ml of 3 M NaSCN-0.2 M Tris-hydrochloride (pH 7.2). After five min., the beads are pelleted (1,000 x g, 5 min., 4° C.), and the antigen-containing supernatant fluid is dialyzed against phosphate-buffered saline (PBS) (pH 7.2). The purity of the preparation is verified by sodium dodecyl sulfate (SDS)-polyacrylamide gel electrophoresis analysis. Typical protein yields from 5 ml infected cell packs are 0.3 mg for HSV-1 gD and HSV-2 gD, 0.4 mg for HSV-1 gC, and 0.01 mg for HSV-2 gF.

Human Sera

A battery of human sera that had been characterized by MN for antibodies to HSV-2 was furnished by Dr. W. Rawls (McMaster Univ., Ontario, Canada). Additional human sera were furnished by Dr. K. Hsu (Columbia Univ.)

Enzyme-Linked Immunosorbent Assay (ELISA)

Purified antigens are diluted 25-50 fold in 0.05M sodium bicarbanate-carbonate coating buffer (pH 9.6) and are adsorbed to wells (100 ul per well) of either U- or flat-bottomed Immulon II microtiter plates (Dynatech Laboratories, Inc.). For detecting antibodies to HSV-2, a mixture consisting of HSV-2 gD (0.2 ug) and HSV-2 gF (0.05 ug) is adsorbed to each well. For detecting antibodies to HSV-1, a mixture consisting of HSV-1 gD (0.2 ug) and HSV-1 gC (0.2 ug) is adsorbed to each well. Adsorption is carried out overnight at 4° C. The wells are washed one time with distilled water and four times with PBS (pH 7.2) containing 0.05% Tween-20 (PBS-T). The protein binding sites are then blocked by adding 200 ul of 5% bovine serum albumin (Miles Laboratories, Inc., Elkhart, Ind.) in PBS (pH 7.2) (BSA-PBS) to each well and incubating for one hour at 37° C. in a humidified box.

Human serum samples are diluted 1:5 with BSA-PBS (final serum dilution tested was 1:10). For assaying antibodies to HSV-2, one serum sample is mixed with an equal voume (100 ul) of HSV-1 infected cell extract diluted 1:10 with BSA-PBS, and a duplicate sample is mixed with an equal volume of uninfected Vero cell extract diluted 1:10 with BSA-PBS. For assaying antibodies to HSV-1, one serum sample is mixed with an equal volume (100 ul) of HSV-2 infected cell extract diluted 1:10 with BSA-PBS, and a duplicate sample is mixed with an equal volume of uninfected Vero cell extract diluted 1:10 with BSA-PBS. Absorptions are carried out for about 30 minutes at room temperature.

Absorbed serum samples (uncentrifuged) are added to microtiter plate wells (50 ul per well) and the plates incubated for 90 minutes at 37° C. in a humidified box. Each well is washed one time with distilled water and four times with PBS-T. To each well is then added 50 ul of peroxidase-conjugated goat anti-human immunoglobulin (Kirkegard and Perry Laboratories, Inc.) diluted 1:200 in 0.5% BSA in PBS-T. The plates are then incubated for 1 hr at 37° C. in a humidified box. The wells are washed five times as above and 100 ul of a color producing substrate solution [150 ug of 2,2'-azino-di-(3-ethyl-benzylthiazoline-sulfonate) (Sigma Chemical Co.) per ml - 0.05 M sodium citrate buffer (pH 4.0) - 0.03% hydrogen peroxide]is added to each well to detect bound peroxidase activity. The plates are incubated in the dark at room temperature for 30 minutes, and the absorbance is measured at 414 nm by a Titertek Multiskan spectrophotometer (Flow Laboratories, Inc.).

EXAMPLE 1

The presence of antibodies against HSV in a 1:10 dilution of human serum was determined by measuring its absorbance index, which is the ratio of absorbance at 414 nm generated by a serum absorbed with an infected cell extract vs. a serum absorbed with an uninfected cell extract. For determining antibodies to HSV-2, the absorbance index for each serum was analyzed to determine a best-fit with MN results furnished by Dr. Rawls for the same sample. Based on this analysis, a best-fit for co-positivity and co-negativity between the screening ELISA test and the reference MN test is observed at an absorbance index of 0.4. A serum was classified as antibody negative if the absorbance at 414 nm was less than 0.5 following absorption with an uninfected cell extract.

For determining antibodies to HSV-1, the data were analyzed for sera which scored negative for HSV-2 antibodies (ratio less than 0.4), but generated an absorbance of 0.5 or greater against HSV-2 antigens when absorbed with an uninfected cell extract (HSV antibody-positive). An absorbance of 0.5 or greater against HSV-1 or HSV-2 antigens generated by a serum absorbed with an uninfected cell extract indicated the presence of antibodies to HSV. Based on this analysis, sera were classified as HSV-1 antibody positive when the ratio of absorbance at 414 nm was 0.5 or greater against HSV-1 target antigens.

To summarize, the presence of antibodies to HSV-1 and HSV-2 was determined by ELISA as follows:

Antibodies to HSV-2:
  Antibody positive when a/b (absorbance index) $\geq 0.4$ and b $\geq 0.5$.
  Antibody negative when a/b $< 0.4$ or when b $< 0.5$.
  where:
  a=absorbance at 414 nm generated by a serum absorbed with an HSV-1 infected cell extract and reacted with a mixture of HSV-2 gD and gF b = absorbance at 414 nm generated by a serum absorbed with an uninfected cell extract and reacted with a mixture of HSV-2 gD and gF.

Antibodies to HSV-1:
Antibody positive when c/d (absorbance index) ≧ 0.5 and d ≧ 0.5
Antibody negative when c/d <0.5 or when d <0.5 where:
c = absorbance at 414 nm generated by a serum absorbed with an HSV-2 infected cell extract and reacted with a mixture of HSV-1 gD and gC
d = absorbance at 414 nm generated by a serum absorbed with an uninfected cell extract and reacted with a mixture of HSV-1 gD and gC.

Statistical Methods: The correlation between the ELISA and MN test results was performed with both the Pearson and the non-parametric Spearman methods. Similar results were obtained by the two methods.

EXAMPLE 2

A battery of 157 human sera was tested by ELISA, and the absorbance index was used to determine the presence or absence of antibodies to HSV-1 and HSV-2 (Table 1). The efficiency of the absorption procedure for removing cross-reactive antibodies was confirmed using hyperimmune rabbit sera made against HSV-1 and HSV-2. A human serum was classified as antibody negative if the absorbance was less than 0.5 following absorption with uninfected cells. For determining antibodies to HSV-2, the absorbance index was compared for best-fit with MN results for the same sera. An index of 0.4 or greater indicated the presence of antibody to HSV-2. When this criterion was applied to a battery of 276 sera, an index of overall agreement of approximately 91% was observed between the screening ELISA test and the reference MN test (Table 2). The degree of co-positivity, defined as the probability that the screening ELISA test will be called positive given that the reference MN diagnosis is positive, was 0.87, while the degree of co-negativity, similarly defined, was 0.93. The correlation between the ELISA and MN tests also was evident when the values obtained in the two tests were analyzed graphically (see the FIGURE). This correlation was highly significant, $p<0.0001$.

The criteria for determining antibodies against HSV-1 were established using a battery of 84 sera (Table 1) which, in the HSV-2 antibody test, showed absorbance indexes of less than 0.4 (HSV-2 antibody negative), yet showed absorbance values of 0.5 or greater following absorption with uninfected cell extracts (HSV antibody positive). When these 84 sera were tested against HSV-1 target antigens and the results were analyzed, 83 of the 84 sera (99%) were classified as HSV-1 antibody-positive based on an absorbance index of 0.5 or greater. When this same criterion was applied to the 31 sera (Table 1) which scored negative for HSV-2 antibodies and also showed absorbance values of less than 0.5 against HSV-2 target antigens following absorption with uninfected cells (HSV antibody-negative), all 31 sera scored negative for antibodies to HSV-1.

EXAMPLE 3

The reproducibility of the ELISA test for determining antibodies against HSV-2 was confirmed by repeated testing of the same sera on different occasions (Table 3). Additional tests run on two separate occasions showed a coefficient of variation of 10% for a battery of eight HSV-1 positive/HSV-2 positive sera, and 26% for a battery of nine HSV-1 positive/HSV-2 negative sera. The same degree of reproducibility was observed with the HSV-1 antibody test.

EXAMPLE 4

HSV-1 gC and gD and HSV-2 gD and gF were used individually as target antigens. While individual proteins could serve effectively as target antigens, the use of mixtures enhanced the sensitivity and specificity of the assay sufficiently to warrant their use.

TABLE 1

Absorbance at 414 nm of Human Sera Tested by ELISA for Antibodies Against HSV-1 and HSV-2

| | Antibodies to HSV-1/Antibodies to HSV-2 | | | |
|---|---|---|---|---|
| | +/+ (n = 37) | +/− (n = 84) | −/+ (n = 5) | −/− (n = 31) |
| Test for HSV-2 | | | | |
| b | 1.48 + 0.26* | 1.29 + 0.35 | 1.57 + 0.16 | 0.11 + 0.11 |
| a/b | 0.66 + 0.19 | 0.20 + 0.09 | 0.86 + 0.05 | NS |
| Test for HSV-1 | | | | |
| d | 1.43 + 0.23 | 1.39 + 0.30 | 1.14 + 0.22 | 0.10 + 0.07 |
| c/d | 0.86 + 0.10 | 0.84 + 0.11 | 0.36 + 0.06 | NS | a - absorbance at 414 nm generated by a serum absorbed with an HSV-1 infected cell extract and reacted with a mixture of HSV-2 gD and gF.
b - absorbance at 414 nm generated by a serum absorbed with an uninfected cell extract and reacted with a mixture of HSV-2 gD and gF.
c - absorbance at 414 nm generated by a serum absorbed with an HSV-2 infected cell extract and reacted with a mixture of HSV-1 gC and gD.
d - absorbance at 414 nm generated by a serum absorbed with an uninfected cell extract and reacted with a mixture of HSV-1 gC and gD.
N = number of sera tested
NS = Not significant. This ratio is unreliable in view of the low value and high relative variability of the denominator.
*Standard Deviation

TABLE 2

Overall Agreement Between MN and ELISA for Determining Antibodies Against HSV-2*

| | | ELISA | | |
|---|---|---|---|---|
| | | + | − | Total |
| MN | + | 111 | 16 | 127 |
| | − | 10 | 139 | 149 |
| | Total | 121 | 155 | 276 |

Overall Agreement $\frac{111 + 139}{276} = 0.91$

*ELISA results were determined as described Example 1. MN results were furnished by Dr. Rawls and were determined by the II/I neutralization index.

TABLE 3

Reproducibility of Results by ELISA for Determining Antibodies to HSV-2

| | Serum #1 (1+/2−) | | Serum #2 (1−/2+) | |
|---|---|---|---|---|
| | b | a/b | b | a/b |
| | 1.581 | 0.32 | 1.759 | 0.83 |
| | 1.515 | 0.23 | 1.640 | 0.90 |
| | 1.300 | 0.19 | 1.389 | 0.94 |
| | 1.409 | 0.26 | 1.242 | 0.80 |
| | 1.332 | 0.31 | 1.415 | 0.89 |
| X̄ | 1.43 | 0.26 | 1.49 | 0.87 |
| S.D. | 0.12 | 0.05 | 0.21 | 0.06 |
| C.V. | 8% | 21% | 14% | 6% | a - absorbance at 414 nm generated by a serum absorbed with an HSV-1 infected cell extract and reacted with a mixture of HSV-2 gD and gF.
b - absorbance at 414 nm generated by a serum absorbed with an uninfected cell extract and reacted with a mixture of HSV-2 gD and gF.
X̄ - mean
S.D. — standard deviation
C.V. — coefficient variation As noted previously, the present invention may be adapted to any of the ELISA techniques. For example, the modifications noted above may be incorporated in assays for antigens (instead of antibodies) or may be used in sandwich-type assays. While the preferred embodiments of this invention have been described, it will be obvious to those skilled in the art that various changes or modifications may be incorporated without departing from the essence of this invention. It is believed, therefore, that all such modifications and changes are integrated in the following claims.

The glycoproteins of this invention have been deposited (in mouse hybridoma cell culture) in the American Type Culture Collection, in Rockville, Md., in the manner requested by the Patent and Trademark Office, i.e., for 30 years and available to the public upon the issuance of a patent. The ascession numbers in the ATCC are: 4S is #HB8683; 19S is #HB8684; and 104S is #HB8685.

We claim:

1. An immunoassay method for determining the presence of antiboides directed against HSV-1 in a biological fluid comprising:
    (a) absorbing said biological fluid with an extract from HSV-2 infected cell culture under conditions wherein intertypic cross-reactive antibodies are removed;
    (b) reacting the biological fluid of step "a" with a target antigen, wherein said target antigen is a purified glycoprotein encoded by HSV-1, and wherein said target antigen specifically binds to antibodies contained in said biological fluid; and
    (c) measuring the amount of antibody bound to said target antigen.

2. A method of claim 1 wherein said target antigen is purified HSV-1 gC or gD or a mixture of gC and gD.

3. An immunoassay method for determining the presence of antibodies directed against HSV-2 in a biological fluid comprising:
    (a) absorbing said biolgical fluid with an extract from HSV-1 infected cell culture under conditions wherein intertypic cross-reactive antibodies are removed;
    (b) reacting the biological fluid of step "a" with a target antigen, wherein said target antigen is a purified glycoprotein encoded by HSV-1, and wherein said target antigen specifically binds to antibodies contained in said biological fluid; and
    (c) measuring the amount of antibody bound to said target antigen.

4. A method of claim 2 wherein said target antigen is purified HSV-2 gD or gF or a mixture of gD and gF.

5. An enzyme-linked immunosorbent assay (ELISA) for diagnosing human infection caused by HSV-1 which comprises:
    (a) immobilizing a target antigen which is a mixture of monoclonal antibody immunoaffinity purifed HSV-1 gC and gD as HSV-1 antigen;
    (b) absorbing human test serum with HSV-2-infected cell culture extract;
    (c) reacting said target antigen with the human test serum of step "b" to form a first antigen-antibody complex;
    (d) reacting said first complex with an enzyme-linked anti-human immunoglobulin to form a second complex;
    (e) reacting said second complex with a color-producing solution specific for the enzyme in step "c";
    (f) repeating steps b–e with a second portion of test serum and extract from non-infected cell culture; and
    (g) measuring the ratio of absorbance generated by the human serum of step "b" to the human serum of step "f".

6. The assay of claim 5 wherein said anti-human immuoglobulin is made in goats.

7. An enzyme-linked immunosorbent assay (ELISA) for diagonosing human infection caused by HSV-2 which comprises:
    (a) immobilizing a target antigen which is a mixture of monoclonal antibody immunoaffinity purified HSV-2 gD and gF as HSV-2 antigens;
    (b) absorbing human test serum with HSV-1-infected cells;
    (c) reacting said target antigen with the human test serum of step "b" to form a first antigen-antibody complex;
    (d) reacting said first complex with an enzyme-linked anti-human immunoglobulin to form a second complex;
    (e) reacting said second complex with a color-producing substraste specific for the enzyme in step "c";
    (f) repeating steps b–e with a second portion of test serum and uninfected cells; and
    (g) measuring the ratio of absorbance generated by the human serum of step "b" to the human serum of step "f."

8. The assay of claim 7 wherein said anti-human immunoglobulin is made in goats.

9. A test kit for assaying antibodies directed against HSV-1 or HSV-2 in human sera which comprises
    (a) microtiter plates coated with purified glycoprotein mixtures encoded by HSV-1 or HSV-2 (target antigens) and treated with a protein solution to prevent further absorption of proteins to the plates by means other than antigen-antibody interaction;
    (b) control positive human serum of known reactivity and antibody titer to HSV-1 or HSV-2 target antigens;
    (c) control negative human serum lacking antibodies to HSV-1 or HSV-2 target antigens;
    (d) uninfected Viro cell extracts for absorption of said human serum;
    (e) HSV-1 infected or HSV-2 infected Viro cell extracts for absorption of said human serum;
    (f) enzyme-conjugated anti-human immunoglobulin;
    (g) color-producing substrate solution for use as a substrate for the enzyme of step f;
    (h) a solution to stop the enzyme reaction; and
    (i) washing buffers and solvent buffers.

* * * * *